United States Patent
Tseng et al.

(10) Patent No.: US 9,714,914 B2
(45) Date of Patent: Jul. 25, 2017

(54) CMOS COMPATIBLE BIOFET

(71) Applicant: Taiwan Semiconductor Manufacturing Co., Ltd., Hsin-Chu (TW)

(72) Inventors: Lee-Chuan Tseng, New Taipei (TW); Che-Ming Chang, Longtan Township (TW); Chung-Yen Chou, Hsinchu (TW); Yuan-Chih Hsieh, Hsinchu (TW)

(73) Assignee: Taiwan Semiconductor Manufacturing Co., Ltd., Hsin-Chu (TW)

( * ) Notice: Subject to any disclaimer, the term of this patent is extended or adjusted under 35 U.S.C. 154(b) by 0 days.

(21) Appl. No.: 14/600,315

(22) Filed: Jan. 20, 2015

(65) Prior Publication Data

US 2016/0209355 A1    Jul. 21, 2016

(51) Int. Cl.
*G01N 27/403* (2006.01)
*G01N 27/414* (2006.01)
*G01N 33/487* (2006.01)
*B82Y 35/00* (2011.01)

(52) U.S. Cl.
CPC .......... *G01N 27/4145* (2013.01); *B82Y 35/00* (2013.01); *G01N 27/414* (2013.01); *G01N 33/48707* (2013.01); *G01N 33/48785* (2013.01); *G01N 27/4148* (2013.01)

(58) Field of Classification Search
CPC .............. G01N 27/414; G01N 27/4145; G01N 27/4148; G01N 33/48707; G01N 33/48785; B82Y 35/00
See application file for complete search history.

(56) References Cited

U.S. PATENT DOCUMENTS

| 5,369,246 A  | 11/1994 | Nanos |
| 7,728,401 B2 | 6/2010  | Takatori |
| 8,405,169 B2 | 3/2013  | Cheng et al. |
| 8,569,808 B1 | 10/2013 | Chen et al. |
| 8,728,844 B1 | 5/2014  | Liu et al. |

(Continued)

OTHER PUBLICATIONS

Toumazou, et al. "Simultaneous DNA amplification and detection using a pH-sensing semiconductor system." Nature Methods, vol. 10, No. 7, Jul. 2013.

(Continued)

*Primary Examiner* — Jesse Y Miyoshi
(74) *Attorney, Agent, or Firm* — Eschweiler & Potashnik, LLC (57) ABSTRACT

The present disclosure relates to an integrated chip having an integrated bio-sensor with a sensing well having one or more sensing well spacers that reduce a size of the sensing well after its formation. In some embodiments, the integrated bio-sensor has a sensing device disposed within a semiconductor substrate. A dielectric structure is disposed onto a first side of the semiconductor substrate. The dielectric structure has an opening with a first width, which is exposed to an ambient environment and that overlies the sensing device. One or more sensing well spacers are arranged on sidewalls of the opening. The one or more sensing well spacers expose a bottom surface of the opening to define a sensing well having a second width that is smaller than the first width.

20 Claims, 9 Drawing Sheets

(56) References Cited

U.S. PATENT DOCUMENTS

| | | | |
|---|---|---|---|
| 8,762,925 | B2 | 6/2014 | Chen et al. |
| 8,791,557 | B2 | 7/2014 | Chang et al. |
| 8,846,416 | B1 | 9/2014 | Chu et al. |
| 8,901,003 | B1 | 12/2014 | Pan |
| 9,528,939 | B2 | 12/2016 | Duer |
| 2002/0017916 | A1 | 2/2002 | Costello |
| 2006/0057771 | A1 | 3/2006 | Kovacs |
| 2006/0197118 | A1* | 9/2006 | Migliorato ....... G01N 33/54373 257/253 |
| 2007/0210350 | A1 | 9/2007 | Omura |
| 2009/0065761 | A1 | 3/2009 | Chen |
| 2010/0230578 | A1 | 9/2010 | Horikoshi et al. |
| 2011/0209555 | A1 | 9/2011 | Ahles |
| 2012/0021918 | A1* | 1/2012 | Bashir ................... B82Y 15/00 506/2 |
| 2012/0032235 | A1 | 2/2012 | Bikumandla |
| 2013/0105868 | A1 | 5/2013 | Kalnitsky et al. |
| 2013/0200438 | A1 | 8/2013 | Liu et al. |
| 2013/0256259 | A1 | 10/2013 | Chang et al. |
| 2013/0293878 | A1 | 11/2013 | Chang et al. |
| 2013/0307626 | A1 | 11/2013 | Mohammadi |
| 2013/0341734 | A1 | 12/2013 | Merz |
| 2014/0073039 | A1 | 3/2014 | Chang et al. |
| 2014/0134748 | A1 | 5/2014 | Liu et al. |
| 2014/0225166 | A1* | 8/2014 | Ellis-Monaghan .. G01N 27/414 257/253 |
| 2014/0256030 | A1 | 9/2014 | Shen et al. |
| 2014/0264467 | A1 | 9/2014 | Cheng et al. |
| 2014/0264468 | A1 | 9/2014 | Cheng et al. |
| 2014/0308752 | A1 | 10/2014 | Chang |
| 2014/0335640 | A1 | 11/2014 | Chang et al. |
| 2014/0370636 | A1* | 12/2014 | Dalton ................. G01N 27/414 438/49 |
| 2015/0129937 | A1 | 5/2015 | Chen et al. |
| 2017/0018626 | A1 | 1/2017 | Hoffman |

OTHER PUBLICATIONS

U.S. Appl. No. 13/480,161, filed May 24, 2012.
Non Final Office Action Dated Feb. 2, 2016 U.S. Appl. No. 14/719,991.
Non Final Office Action Dated Jul. 18, 2016 U.S. Appl. No. 14/713,543.
Mahdavifar, et al. "Implementation of a Polysilicon Micro Electro-Thermal Detector in Gas Chromatography System with Applications in Portable Environmental Monitoring." ECS Journal of Solid State Science and Technology, 4 (10) S3062-S3066 (2015). Aug. 28, 2015.
Scorzoni, et al. "Thermal Characterization of a Thin Film Heater on Glass Substrate for Lab-on-Chip Applications." 2014 IEEE International Instrumentation and Measurement Technology Conference (I2MTC) Proceedings. May 12, 2014.
U.S. Appl. No. 15/216,853, filed Jul. 22, 2016.
Final Office Action Dated Aug. 12, 2016 U.S. Appl. No. 14/719,991.
Jang, et al. "Performance Enhancement of Capacitive-Coupling Dual-Gate Ion-Sensitive Field-Effect Transistor in Ultra-Thin-Body." Scientific Reports, 4: 5284. Published Jun. 13, 2014.
Romero-Garcia, et al.; "Silicon Nitride CMOS-compatible Platform for Integrated Photonics Applications at Visible Wavelengths;" Optics Express, vol. 21, No. 12, Jun. 17, 2013, p. 1-11.
Salm, et al. "Ultralocalized Thermal Reactions in Subnanoliter Droplets-in-air;" PNAS; vol. 110; No. 9; Feb. 26, 2013; p. 3310-3315.
"Supporting Information for Ultralocalized Thermal Reactions in Subnanoliter Droplets-in-air;" PNAS, vol. 110; No. 9, Feb. 26, 2013, p. 1-25.
Lee, et al.; "Microchip-based one step DNA Extraction and Real-Time PCR in one Chamber for Rapid Pathogen Identification;" Lab Chip; The Royal Society of Chemistry 2006; p. 886-895.
Dametto, Paolo; "DNA Amplification and Detection Using a pH-Sensing System: Implications for Current Analytical Technologies and Point-of-Care Nucleic Acid Tests;" Aug. 2013; p. 1-31.
Bhattacharya, et al.; "PCR-Based Detection in a Micro-Fabricated Platform;" Lab Chip; The Royal Society of Chemistry; 2008; p. 1130-1136.
Non Final Office Action Dated Feb. 14, 2017 U.S. Appl. No. 15/216,853.
Petrucci, et al. "Thermal Characterization of Thin Film Heater for Lab-On-Chip Application." 2015 XVIII AISEM Annual Conference. Feb. 2015.
Nanohelix.net RealHelix qPCR Kit. Published in 2009. Retrieved online at http://www.nanohelix.net/02_products/view.asp?pack_code=277.
U.S. Appl. No. 15/386,545, filed Dec. 21, 2016.

* cited by examiner

CMOS COMPATIBLE BIOFET

BACKGROUND

In recent years, the semiconductor industry has developed integrated chips (ICs) having integrated bio-sensors configured to detect the presence of certain biomarkers in an ambient environment (e.g., in a patient's blood stream). Biosensors are analytical devices that convert a biological response into an electrical signal. For example, bio-sensors can generate electrical signals that identify and detect different analytes such as toxins, hormones, DNA strands, proteins, bacteria, etc., in a variety of applications such as molecular diagnostics, pathogen detection, and environmental monitoring.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

Integrated bio-sensors normally comprise a sensing device disposed within a semiconductor substrate. The sensing device is often a transistor device (e.g., a MOSFET) having a gate terminal that is electrically coupled to a sensing membrane. The sensing membrane is disposed within a sensing well formed within a dielectric material disposed over the semiconductor substrate. The sensing well is configured to act as a receptacle for a liquid to be analyzed. During operation, analytes from the liquid will interact with a sensing molecule (e.g., a chemical or biological recognition element) that attaches the analyte to the sensing membrane. Upon being attached to the sensing membrane, the analytes will vary electrical operation of the sensing device, thereby indicating a presence of analytes in the liquid.

It is desirable to decrease the size of the sensing wells so that bio-sensors can be fit within smaller areas of an integrated chip and/or so that more sensing devices can fit within an array. While dry etching processes are able to form sensing wells having relatively small dimensions, such dry etching processes may cause plasma damage to a sensing device of a resulting bio-sensor. Wet etching processes may alternatively or additionally be used to form the sensing wells. However, such wet etching processes have a limited critical dimension control that can prevent a relatively small sensing well size from being achieved.

Accordingly, the present disclosure relates to an integrated chip having an integrated bio-sensor with a sensing well comprising one or more sensing well spacers that are configured to reduce a size of the sensing well after its formation. In some embodiments, the integrated bio-sensor comprises a sensing device disposed within a semiconductor substrate. A dielectric structure is disposed onto a first side of the semiconductor substrate. The dielectric structure has an opening with a first width, which is exposed to an ambient environment and that overlies the sensing device. One or more sensing well spacers are arranged on sidewalls of the opening. The one or more sensing well spacers expose a bottom surface of the opening to define a sensing well having a second width that is smaller than the first width. The sensing well spacers allow for a sensing well to be formed using a wet etching process, and then subsequently shrunk, thereby providing for a sensing well having a relatively small size that does not suffer from plasma damage caused by a dry etching process.

Figure 1:
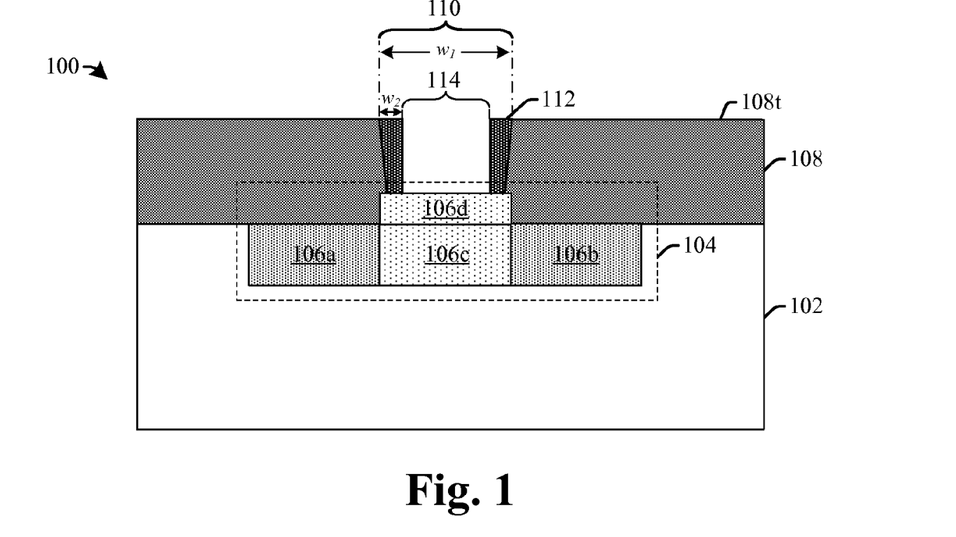
FIG. 1 illustrates a cross-sectional view of some embodiments of an integrated bio-sensor having a sensing well comprising one or more sensing well spacers.

FIG. 1 illustrates a cross-sectional view of some embodiments of an integrated bio-sensor 100 having a sensing well 114 comprising one or more sensing well spacers 112.

The integrated bio-sensor 100 comprises a sensing device 104 arranged within a semiconductor substrate 102. In some embodiments, the sensing device 104 may comprise a transistor device having a source region 106a and a drain region 106b separated by a channel region 106c. A gate region 106d is configured to control the flow of charge carriers (e.g., holes and/or electrons) within the channel region 106c during operation of the transistor device.

A dielectric structure 108 is disposed over the semiconductor substrate 102. The dielectric structure 108 comprises one or more layers of dielectric material (e.g., silicon-dioxide). The dielectric structure 108 comprises an opening 110 disposed within a top surface 108t of the dielectric structure 108. The opening 110 is a cavity or negative relief that vertically extends from a top surface 108t of the dielectric structure 108 to a position abutting the gate region 106d.

One or more sensing well spacers 112 are located on sidewalls of the opening 110. The one or more sensing well spacers 112 are laterally positioned between the dielectric structure 108 and a sensing well 114 disposed within the opening 110. The sensing well spacers 112 define a size of the sensing well 114. For example, if integrated chip 100 has an opening 110 with a width of $w_1$ and sensing well spacers 112 with widths of $w_2$, the overall width of the sensing well 114 will be $w_1$-$2w_2$. In some embodiments, the opening 110 may have a width $w_1$ that is in a range of between approximately 400 nm and approximately 800 nm, while the sensing well spacers 112 may respectively have widths $w_2$ that are in a range of between approximately 50 nm and approximately 300 nm. In other embodiments, the opening 110 and the sensing well spacers 112 may have larger or smaller widths.

In some embodiments, the sensing well spacers 112 may vertically extend from a top surface 108t of the dielectric structure 108 to a position abutting the gate region 106d. Although, the sensing well spacers 112 are illustrated in the cross-sectional view of bio-sensor 100 as being laterally separated from one another, it will be appreciated that the sensing well spacers 112 may form a continuous structure around an interior sidewall surface of the sensing well 114. For example, if opening 110 has a circular shape, the sensing well spacers 112 may be disposed in the opening 110 as a circular layer abutting an interior surface of the opening.

The sensing well 114 allows for fluids to come into contact with the gate region 106d of the sensing device 104, thereby allowing the sensing device 104 to detect analytes within the fluid (e.g., ion concentrations, photon concentrations, DNA sequences, etc.) based upon changes in electric potential change around the gate region 106d (e.g., based upon a change in electric charge around the extended gate electrode determined by Poisson's equal or based upon a chemical equilibrium potential determined by the Nernest equation). For example, during operation, a first biologically sensitive element such as a first enzyme may be introduced into the sensing well 114. The first enzyme is immobilized onto the gate region 106d, thereby enabling the sensing device 104 to detect a first analyte associated with the first enzyme.

By using the sensing well spacers 112 to define the size of the sensing well 114, integrated bio-sensor 100 is able to have a sensing well 114 with a relatively small size (e.g., having a width less than 500 nm) without the negative effects (e.g., plasma damage) associated with dry plasma etching. This is because, while wet etchants are typically not able to form small sensing wells due to their inability to achieve small critical dimension control, the use of the one or more sensing well spacers 112 mitigates this problem by forming an opening 110 having a larger CD dimension using a wet etchant, and then subsequently shrinking the opening 110 to form the sensing well 114 by using the one or more sensing well spacers 112. Accordingly, the bio-sensor 100 may have a sensing well 114 with a small critical dimension and a sensing device 104 without plasma damage.

Figure 2:
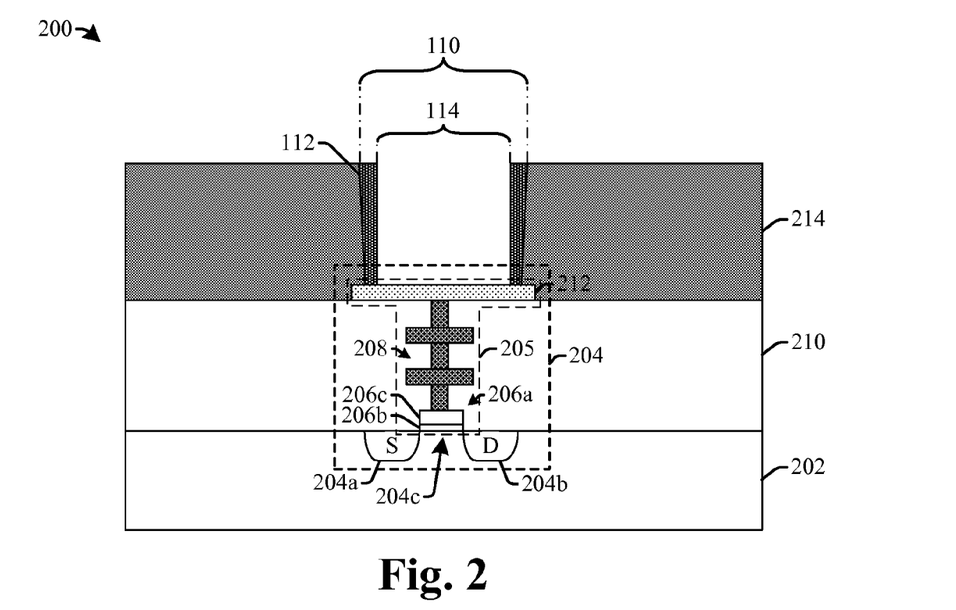
FIGS. 2-3 illustrate a cross-sectional view of some alternative embodiments of integrated bio-sensors having sensing wells comprising one or more sensing well spacers.

FIG. 2 illustrates a cross-sectional view of some alternative embodiments of an integrated bio-sensor 200 having a sensing well 114 comprising one or more sensing well spacers 112.

The integrated bio-sensor 200 has a sensing device 204 comprising a MOSFET device disposed within a semiconductor substrate 202. The MOSFET device comprises a source region 204a and a drain region 204b laterally separated by a channel region 204c. The MOSFET device further comprises an extended gate region 205 having a gate region 206a with a gate dielectric layer 206b (e.g., a silicon dioxide ($SiO_2$) layer, a high-k dielectric layer, etc.) and an overlying gate electrode 206c, one or more metal interconnect layers 208 disposed within an inter-level dielectric (ILD) layer 210 at a position overlying the gate region 206a, and a sensing membrane 212 overlying the one or more metal interconnect layers 208.

The sensing membrane 212 comprises a material that causes the electrical properties of the sensing device 204 to change in the presence of an analyte, thereby allowing the sensing device 204 to detect the presence of the analyte. In various embodiments, the sensing membrane 212 may comprise a high-k dielectric material (e.g., silicon nitride ($Si_3N_4$), aluminum oxide ($Al_2O_3$), titanium oxide ($TiO_2$), hafnium oxide ($HfO_2$), tantalum pentoxide ($Ta_2O_5$), tin oxide (SnO), tin dioxide ($SnO_2$), $BaxSr_{1-x}TiO_3$ (BST)), a conductive material (e.g., TiN), or a combination thereof (e.g., a high-k dielectric material disposed over a conductive material).

A dielectric structure 214 is disposed over the ILD layer 210. An opening 110 is arranged within the dielectric structure 214 at a position overlying the sensing membrane 212. One or more sensing well spacers 112 are disposed within the opening 110 to define a sensing well 114. The sensing well 114 extends from a top surface of the dielectric structure to a top surface of the sensing membrane 212. In some embodiments, a sensing enhancement layer (e.g., a high-k dielectric layer) may be disposed onto a bottom surface of the sensing well 114 at a position laterally arranged between the one or more sensing well spacers 112.

Figure 3:
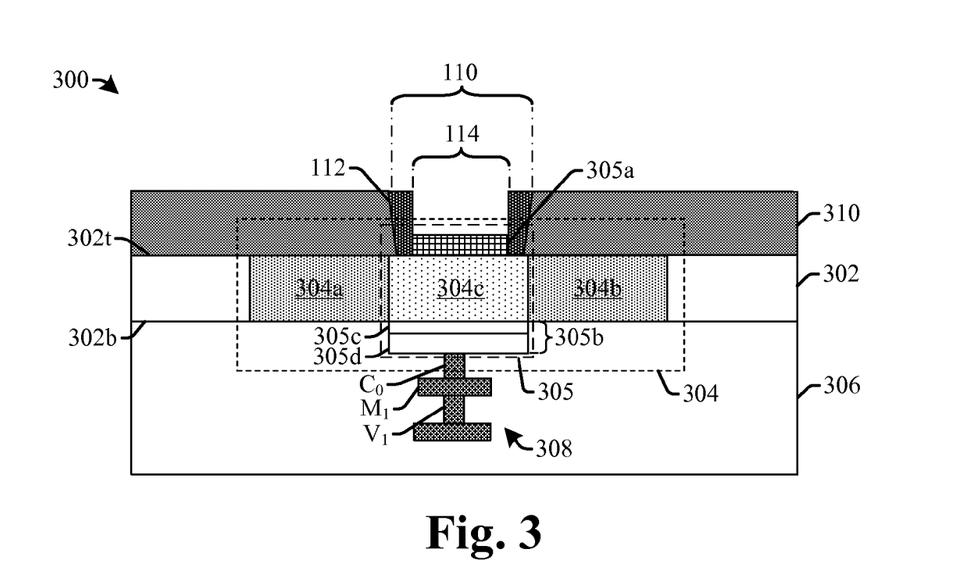

FIG. 3 illustrates a cross-sectional view of some alternative embodiments of an integrated bio-sensor 300 having a sensing well 114 comprising one or more sensing well spacers 112.

The integrated bio-sensor 300 comprises an active silicon layer 302 abutting a buried oxide layer 310 (e.g., a silicon dioxide layer) on a first side 302t and further abutting an inter-level dielectric (ILD) layer on a second side 302b, opposing the first side 302t. A transistor device 304 is disposed within the active silicon layer 302. The transistor device 304 has a source region 304a and a drain region 304b laterally separated by a channel region 304c. A gate region 305 is laterally arranged between a source region 304a and a drain region 304b.

In some embodiments, wherein the transistor device 304 comprises a dual gate (DG) ISFET (ion-sensitive field-effect transistor), the gate region 305 may comprises a front gate region 305a and a back gate region 305b disposed on opposing sides of the channel region 304c. In such embodiments, the front gate region 305a may comprise a first gate dielectric layer disposed between the sensing well 114 and the channel region 304c. In some embodiments, the first gate dielectric material may comprise a high-k gate dielectric material. In some embodiments, the first gate dielectric layer separates the channel region 304c from a first gate electrode (not shown) that is in communication with a fluid in the sensing well 114. The back gate region 305b comprises a second gate electrode 305d that is vertically separated from the channel region 304c by way of a second gate dielectric layer 305c. In some embodiments, capacitive-coupling between the front gate region 305a and the back gate region 305b may amplification a response of the transistor device 304 (e.g., of the Nernst response).

The back gate region 305b is connected to one or more metal interconnect layers 308 disposed within one or more dielectric materials of the ILD layer 306. In some embodiments, the one or more metal interconnect layers 308 may comprise a conductive contact $C_O$ configured to connect the sensing device $C_O$ to one or more metal wires $M_x$ (x=1, 2, 3, 4) that are vertically interconnected by way of one or more metal vias $V_x$ (x=1, 2, 3). In some embodiments, the conductive contact $C_O$, the metal vias $V_x$, and the metal wire $M_x$ may comprise tungsten, copper, or aluminum.

An opening 110 is arranged within the buried oxide layer 310 at a position overlying the front gate region 305a. One or more sensing well spacers 112 are disposed within the opening 110 to define a sensing well 114. In some embodiments, the sensing well 114 and the sensing well spacers 112 may abut the front gate region 305a.

Figure 4:
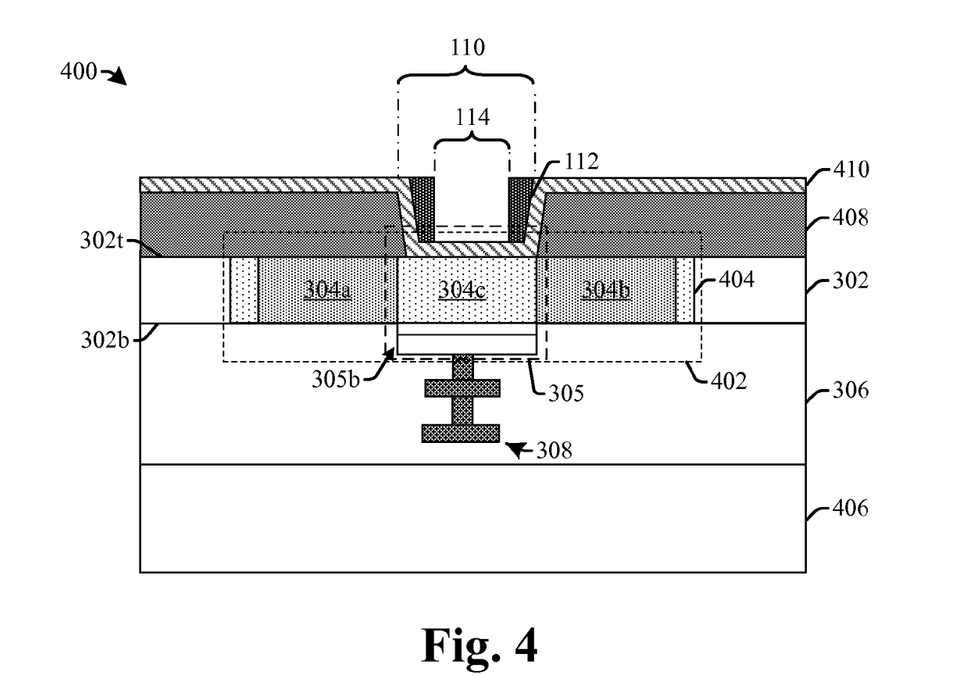
FIG. 4 illustrates a cross-sectional view of some additional embodiments of an integrated bio-sensor having a sensing well comprising one or more sensing well spacers.

FIG. 4 illustrates a cross-sectional view of some additional embodiments of an integrated bio-sensor 400 having a sensing well 114 comprising one or more sensing well spacers 112.

The integrated bio-sensor 400 comprises a transistor device 402 disposed within an active silicon layer 302 abutting a buried oxide layer 310 (e.g., a silicon dioxide layer) on a first side 302t and further abutting an inter-level dielectric (ILD) layer 306 on a second side 302b, opposing the first side 302t. The transistor device 402 has a source region 304a and a drain region 304b having a first doping type (e.g., n-type). A channel region 304c, having a second doping type different than the first doping type, is laterally arranged between the source region 304a and the drain region 304b. In some embodiments, the source region 304a and the drain region 304b may be disposed within a well region 404 having the first doping type and a doping concentration greater than that of the active silicon layer 302.

A plurality of metal interconnect layers 308 are disposed within the ILD layer 306 having one or more dielectric materials. In some embodiments, the one or more dielectric materials may comprise a low-k dielectric layer, an ultra low-k dielectric layer, an extreme low-k dielectric layer, and/or a silicon dioxide layer. A handle substrate 406 (e.g., a silicon carrier substrate) abuts a bottom surface of the ILD layer 306. The handle substrate 406 comprises a rigid structure that provides structural support a remainder of the integrated chip. In some embodiments, the handle substrate 406 may comprise a silicon wafer having a thickness greater than approximately 200 um.

A high-k dielectric layer 410 may be disposed over the active silicon layer 302 and the buried oxide layer 408. The high-k dielectric layer 410 abuts sidewalls of the sensing well 114 so as to continuously extend from the bottom surface of the sensing well 114 to a top surface of the buried oxide layer 408. In some embodiments, the high-k dielectric layer 410 may comprise a high-k dielectric layer having a dielectric constant greater than 3.9. For example, in some embodiments, the high-k dielectric layer 410 may comprise a hafnium oxide (HfO) layer. In some embodiments, the high-k dielectric layer 410 may comprise a front gate region (e.g., corresponding to 305a of FIG. 3) of the transistor device 402.

Sensing well spacers 112 are disposed within the sensing well 114 at positions above the high-k dielectric layer 410. This causes the high-k dielectric layer 410 to vertically separate the sensing well spacers 112 from the active silicon layer 302 and to laterally separate the sensing well spacers 112 from the buried oxide layer 408. The sensing well spacers 112 are laterally set back (i.e., laterally separated) from the source region 304a and the drain region 304b. The sensing well spacers 112 have top surfaces that are substantially aligned with a top surface of the high-k dielectric layer 410, so that the sensing well spacers 112 have a height that is substantially equal to that of the buried oxide layer 408.

The sensing well spacers 112 comprise a material that has a relatively large etching selectivity compared to the underlying high-k dielectric layer 410 (i.e., the sensing well spacers 112 comprise a material that is etched at a higher (i.e., faster) etching rate than the high-k dielectric layer 410). In some embodiments, the sensing well spacers 112 may comprise a material that etches at a rate of greater than 5 times faster than the high-k dielectric layer 410 (i.e. the sensing well spacers 112 comprise a material having an etching selectivity of greater than 5 with respect to the high-k dielectric layer 410). In other embodiments, the sensing well spacers 112 may comprise a material that etches at a rate of greater than 20 times faster than the high-k dielectric layer 410. In some embodiments, the sensing well spacers 112 may comprise an oxide or a nitride (e.g., silicon nitride).

Figure 5:
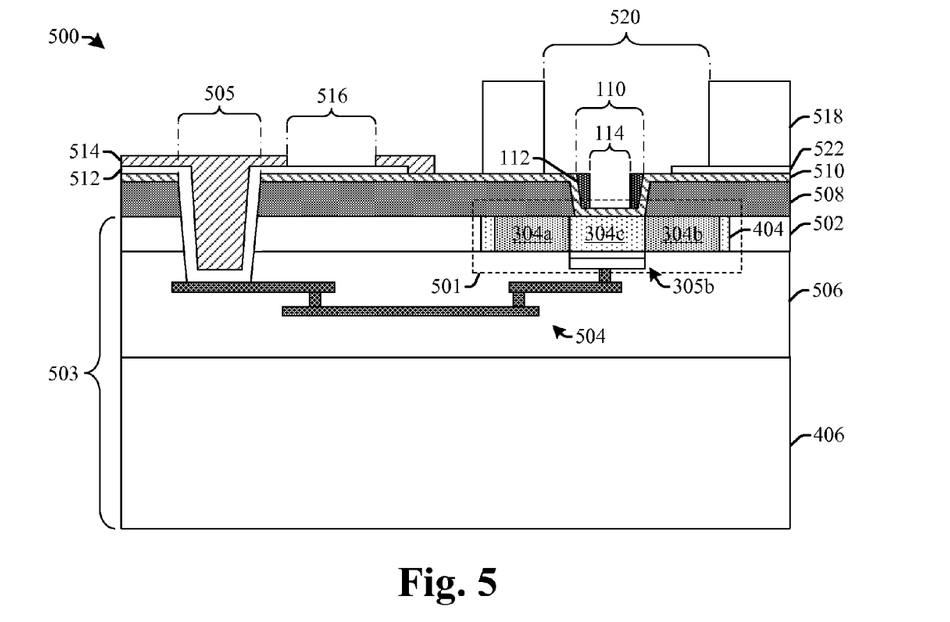
FIG. 5 illustrates a cross-sectional view of some embodiments of an integrated chip comprising an integrated bio-sensor having a sensing well comprising one or more sensing well spacers.

FIG. 5 illustrates a cross-sectional view of some embodiments of an integrated chip 500 having an integrated bio-sensor 501 with a sensing well 114 comprising one or more sensing well spacers 112.

The integrated chip 500 comprises a wire-bonding well 505 disposed within a semiconductor substrate 503 at a position that is laterally separated from an integrated bio-sensor 501. The semiconductor substrate 503 comprises a buried oxide layer 508, an active silicon layer 502, an ILD layer 506, and a handle substrate 406. The wire-bonding well 505 vertically extends from a top of the buried oxide layer 508, through the active silicon layer 502 to an upper one of a plurality of metal interconnect layers 504 within the ILD layer 306.

In some embodiments, a high-k dielectric layer 510 is disposed over the top surface of the buried oxide layer 508. A wire-bond redistribution layer 512 is disposed over the high-k dielectric layer 510 and extends into the wire-bonding well 505 to a position that abuts sidewalls of the buried oxide layer 508, the active silicon layer 502, and the ILD layer 506, and that further abuts a top surface of the upper one of the plurality of metal interconnect layers 504. The wire-bond redistribution layer 512 is configured to provide for a conductive path that extends from a bottom of the wire-bonding well 505 to a top of the buried oxide layer 508. In some embodiments, the wire-bond redistribution layer 512 may comprise copper or aluminum.

One or more dielectric structures 514 are disposed onto the wire-bond redistribution layer 512. The one or more dielectric structures 514 define a wire-bonding area 516 on a top surface of the wire-bond redistribution layer 512. In some embodiments, the one or more dielectric structure 514 may comprise silicon dioxide ($SiO_2$), for example. The plurality of metal interconnect layers 504 are configured to electrically connect the wire-bond redistribution layer 512 to the integrated bio-sensor 501. For example, the plurality of metal interconnect layers 504 may contact the wire-bond redistribution layer 512 at a bottom of the wire-bonding well 505 and may laterally connect the wire-bond redistribution layer 512 to the back gate region 305b of the integrated bio-sensor 501.

In some embodiments, a fluidic channel 520 is arranged over and is in communication with the sensing well 114. The fluidic channel 520 may comprise a channel that is defined by one or more channel definition structures 518. In some embodiments, the one or more channel definition structures 518 may comprise silicon or a polymer, such as polydimethylsiloxane (PDMS), for example. In some embodiments, a conductive layer 522, configured to act as a front gate electrode (electrically insulated from channel region 304c by high-k dielectric layer 410), may extend into the fluidic channel 520. In some embodiments, the conductive layer 522 is vertically arranged between the high-k dielectric layer 510 and the one or more channel definition structures 518 at a position overlying the buried oxide layer 508.

Figure 6:
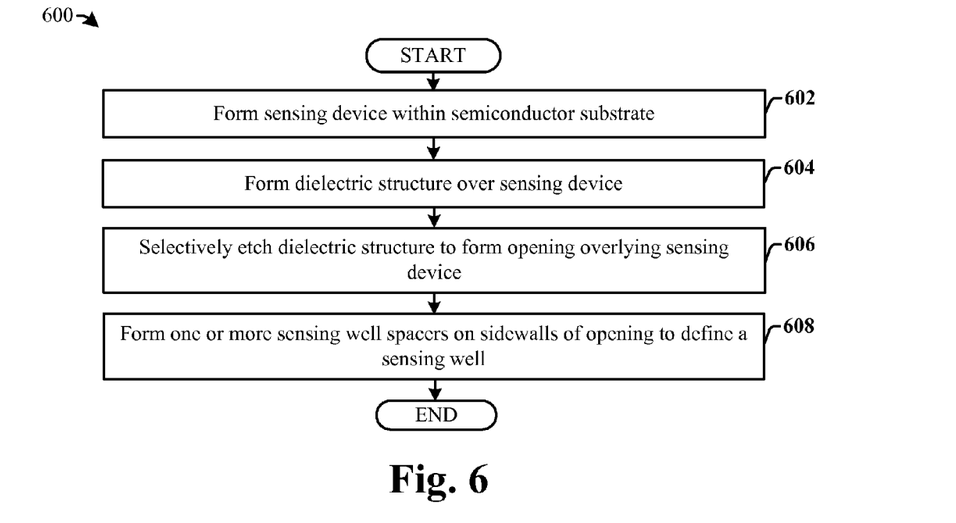
FIG. 6 illustrates a flow diagram of some embodiments of a method of forming an integrated bio-sensor having a sensing well comprising one or more sensing well spacers.

FIG. 6 illustrates a flow diagram of some additional embodiments of a method 600 of forming an integrated chip comprising an integrated bio-sensor having a sensing well with sensing well spacers.

While disclosed methods (e.g., methods 600 and 700) are illustrated and described herein as a series of acts or events, it will be appreciated that the illustrated ordering of such acts or events are not to be interpreted in a limiting sense. For example, some acts may occur in different orders and/or concurrently with other acts or events apart from those illustrated and/or described herein. In addition, not all illustrated acts may be required to implement one or more aspects or embodiments of the description herein. Further, one or more of the acts depicted herein may be carried out in one or more separate acts and/or phases.

At 602, a sensing device is formed within a substrate. In some embodiments, the sensing device may comprise a transistor device, such as a MOSFET or an ISFET, for example. The semiconductor substrate may comprise any type of semiconductor body (e.g., silicon, SiGe, SOI) such as a semiconductor wafer and/or one or more die on a wafer, as well as any other type of semiconductor and/or epitaxial layers associated therewith.

At 604, a dielectric structure is formed over the sensing device.

At 606, the dielectric structure is selectively etched to form an opening overlying the sensing device.

At 608, one or more sensing well spacers are formed onto sidewalls of the opening to define a sensing well.

Figure 7:
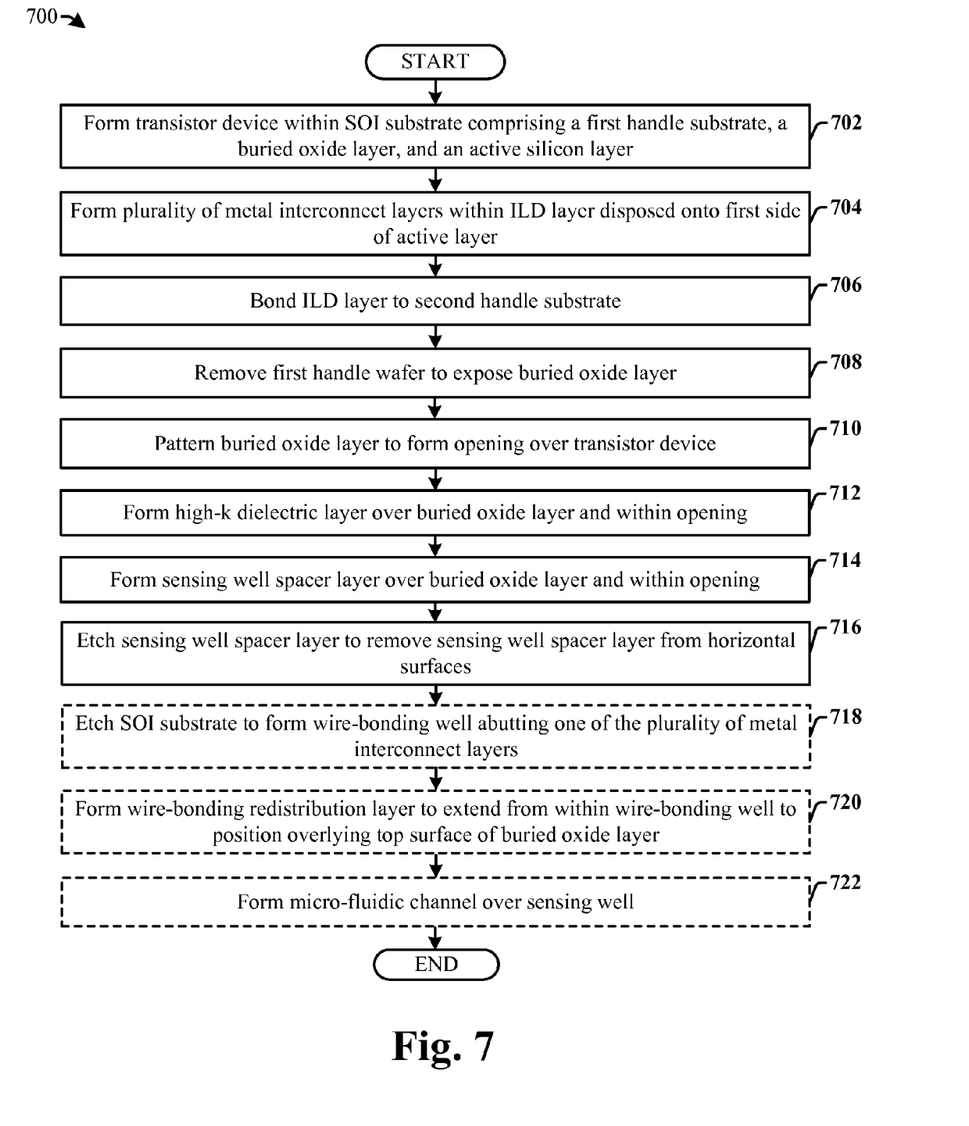
FIG. 7 illustrates a flow diagram of some additional embodiments of a method of forming an integrated chip comprising an integrated bio-sensor having a sensing well comprising one or more sensing well spacers.

FIG. 7 illustrates a flow diagram of some additional embodiments of a method 700 of forming an integrated chip comprising an integrated bio-sensor having a sensing well with sensing well spacers.

At 702, a transistor device (e.g., a MOSFET, an ISFET, etc.) is formed within a silicon-on-insulator (SOI) substrate comprising a first handle substrate, a buried oxide layer, and an active silicon layer.

At 704, a plurality of metal interconnect layers are formed within an ILD layer formed onto a first side of the active silicon layer. In some embodiments, the ILD layer may comprise one or more dielectric materials.

At 706, the ILD layer is bonded to a second handle substrate.

At 708, the first handle substrate is removed to expose the buried oxide layer.

At 710, the buried oxide layer is patterned, to form an opening in the dielectric structure arranged over the transistor device. In some embodiments, the buried oxide layer may be patterned using a wet etching process.

At 712, a high-k dielectric layer is formed over the buried oxide layer and within the opening.

At 714, a sensing well spacer layer is formed over the buried oxide layer and within the opening.

At 716, the sensing well spacer layer is etched to remove the sensing well spacer layer from horizontal surfaces of the substrate.

At 718, the SOI substrate is etched to form a wire-bond opening abutting one of the plurality of metal interconnect layers.

At 720, a wire-bond redistribution layer is formed over the SOI substrate to extend from a first position within the wire-bonding well to a second position overlying a top surface of the buried oxide layer.

At 722, a micro-fluidic channel is formed over the sensing well.

FIGS. 8-17 illustrate some embodiments of cross-sectional views showing a method of forming an integrated chip comprising an integrated bio-sensor having a sensing well comprising a sensing membrane with a roughened surface. Although FIGS. 8-17 are described in relation to method 700, it will be appreciated that the structures disclosed in FIGS. 8-17 are not limited to such a method, but instead may stand alone as structures independent of the method.

Figure 8:
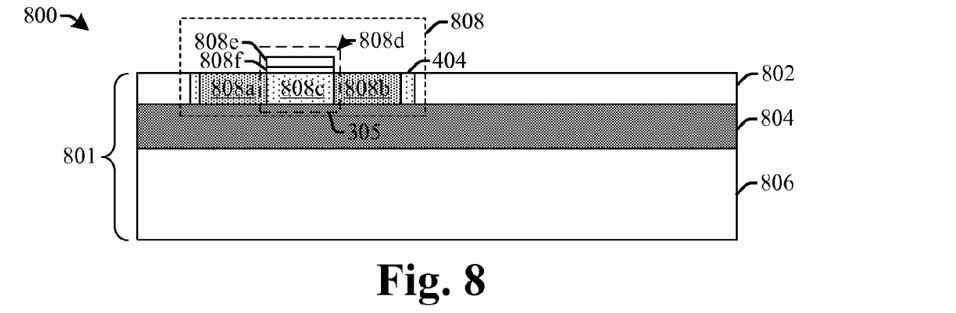
FIGS. 8-17 illustrate some embodiments of cross-sectional views showing a method of forming an integrated chip comprising an integrated bio-sensor having a sensing well comprising one or more sensing well spacers.

FIG. 8 illustrates some embodiments of a cross-sectional view 800 of an integrated chip corresponding to act 702.

As shown in cross-sectional view 800, a transistor device 808 is formed within a semiconductor substrate 801. In some embodiments, the semiconductor substrate 801 may comprise an SOI substrate having a first handle substrate 806 (e.g., a silicon handle wafer), a buried oxide layer 804, and an active silicon layer 802. In some embodiments, the transistor device 808 may comprise a MOSFET having a source region 808a, a drain region 808b that is separated from the source region 808a by a channel region 808c, and a gate region 808d comprising a gate electrode 808e separated from the channel region 808c by a gate dielectric layer 808f. In other embodiments (not shown), the transistor device 808 may comprise a dual gate ISFET having a gate region comprising a front gate region and a back gate region disposed on opposing sides of the channel region 808c.

In some embodiments, the source region 808a and the drain region 808b may be formed by implanting dopant species (e.g., boron or phosphorus) into the active silicon layer 802 at a high energy. In some embodiments, the dopants may be subsequently driven into the active silicon layer 802 using a high temperature anneal. The gate region 808d is formed over the channel region 808c by deposition processes and one or more subsequent patterning processes.

Figure 9:
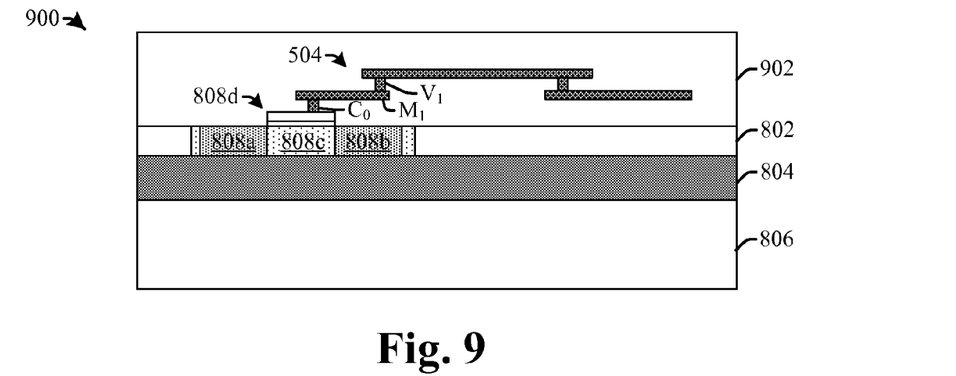

FIG. 9 illustrates a cross-sectional view 900 of an integrated chip corresponding to act 704.

As shown in cross-sectional view 900, an inter-level dielectric (ILD) layer 902 comprising one or more dielectric materials is formed onto the active silicon layer 802. A plurality of metal interconnect layers 504 are formed within the ILD layer 902. The ILD layer 902 may comprise one or more of a low-k dielectric layer, an ultra-low-k dielectric layer, and/or an oxide layer. In some embodiments, the ILD layer 902 may be deposited by way of a vapor deposition technique (e.g., physical vapor deposition, chemical vapor deposition, etc.). The plurality of metal interconnect layers 504 may comprise a contact $C_0$ formed within a first dielectric material at a position overlying and electrically connected to the gate region 808d, one or more metal wire layers $M_x$ configured to provide lateral interconnections, and one or more metal via layers $V_x$ configured to provide vertical interconnections.

In some embodiment, the plurality of metal interconnect layers 504 may be formed by selectively exposing the ILD layer 902 to an etchant configured to selectively etch the ILD layer 902 to form a plurality of openings. A metal material (e.g., tungsten, aluminum, and/or copper) is subsequently formed within the plurality of openings. In various embodiments, the etchant may comprise a dry etchant have an etching chemistry comprising a fluorine species (e.g., $CF_4$, $CHF_3$, $C_4F_8$, etc.) or a wet etchant comprising hydroflouric acid (HF), for example.

Figure 10:
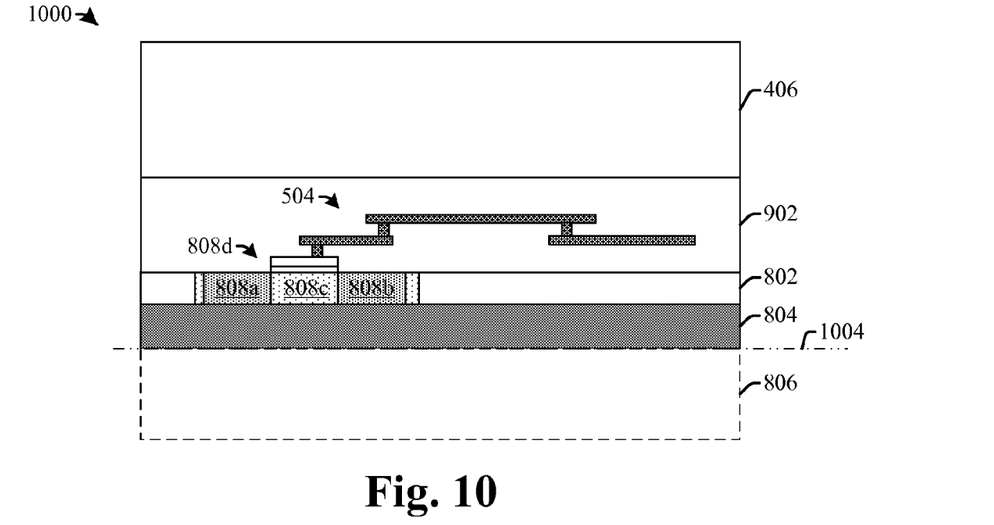

FIG. 10 illustrates a cross-sectional view 1000 of an integrated chip corresponding to acts 706-708.

As shown in cross-sectional view 1000, the first handle substrate 806 is removed and the ILD layer 902 is bonded to a second handle substrate 406 (i.e., a carrier substrate) configured to provide support to the integrated chip. The first handle substrate 806 is removed from the substrate to expose the buried oxide layer 804. In various embodiments, the first handle substrate 806 may be removed by a chemical mechanical polishing (CMP) process (along line 1004) or by an etching process.

Figure 11:
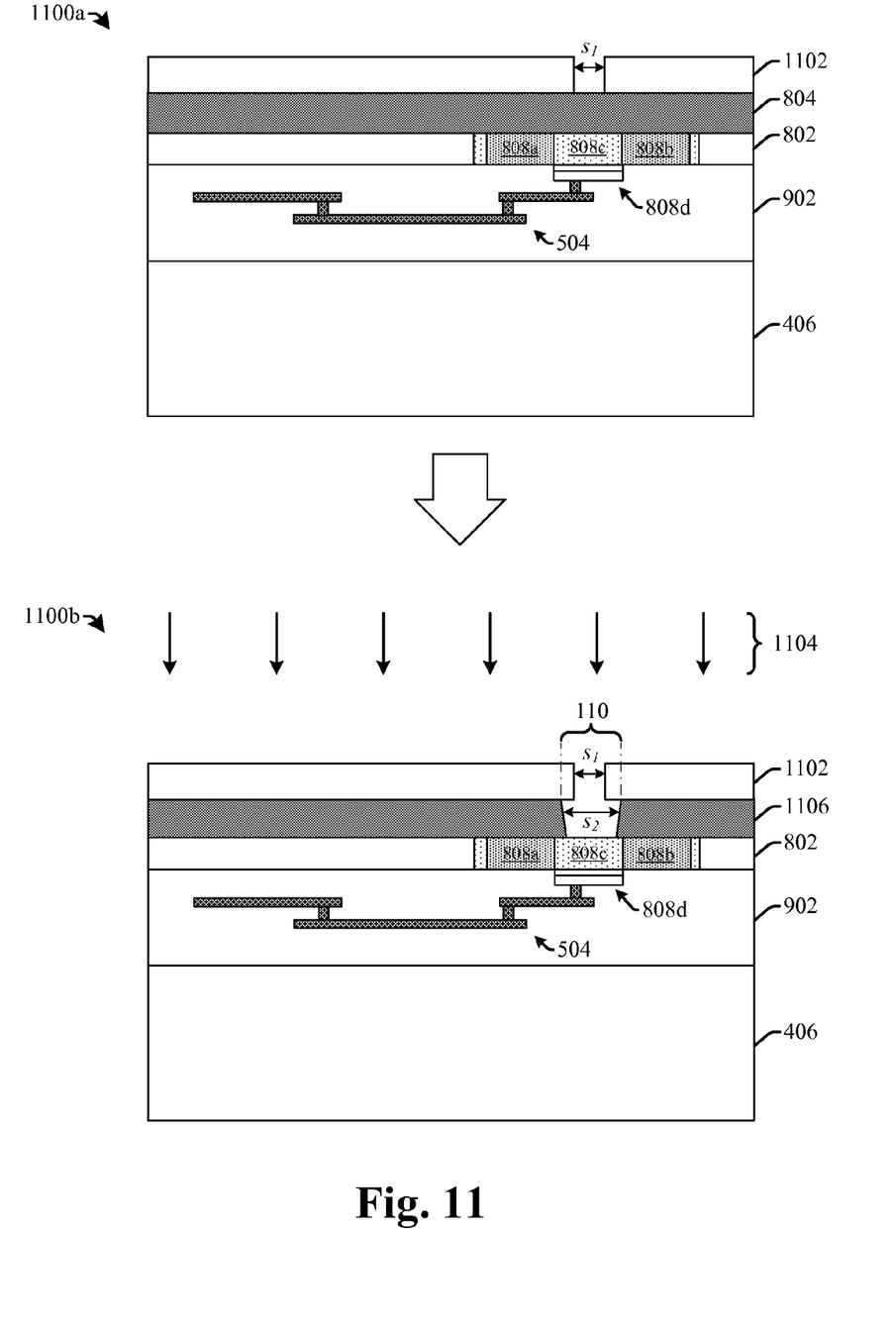

FIG. 11 illustrates some embodiments of a cross-sectional views, 1100a and 1100b, of an integrated chip corresponding to act 710.

As shown in cross-sectional view 1100a, a masking layer 1102 is selectively formed over the buried oxide layer 804. The masking layer 1102 defines a position of an opening 110 within the buried oxide layer 804. In some embodiments, the masking layer 1102 may comprise a photoresist layer patterned according to a photolithography process. In other embodiments, the masking layer 1102 may comprise a hardmask layer (e.g., SiN) patterned according to a dry etching process (e.g., having an etching chemistry comprising $CF_4$, $CHF_3$, $C_4F_8$, HF, etc.)

As shown in cross-sectional view 1100b, the buried oxide layer 1106 is selectively etched according to the masking layer 1102 using a wet etchant 1104. The wet etchant 1104 forms an opening 110 in the buried oxide layer 1106 having a width of $s_2$. In some embodiments, the width $s_2$ is greater than the width $s_1$ of an opening in the masking layer 1102. In some embodiments, the wet etchant 1104 may comprise a buffered hydroflouric (HF) acid solution.

Figure 12:
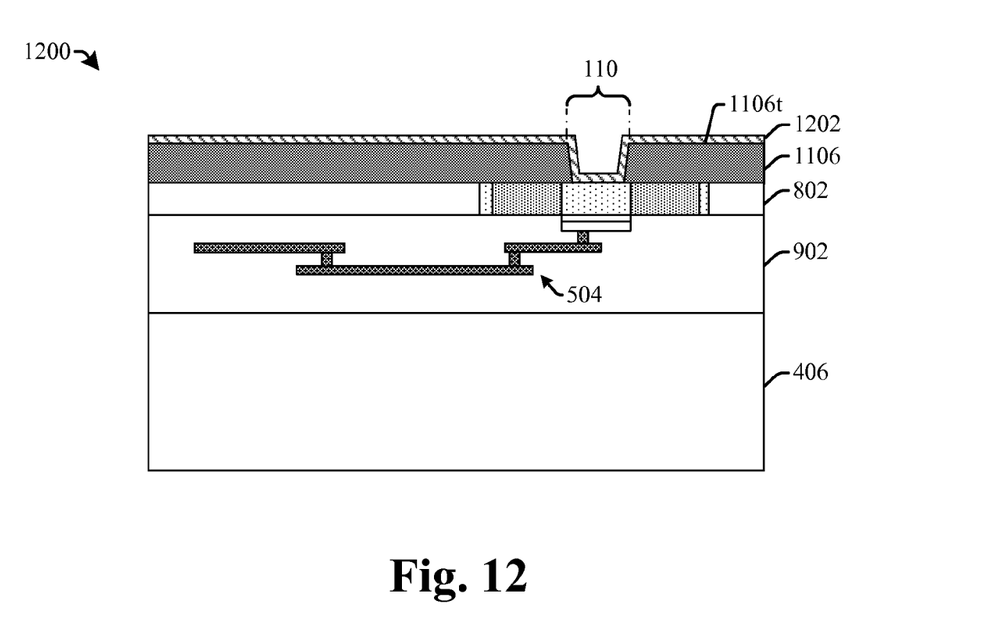

FIG. 12 illustrates some embodiments of a cross-sectional view 1200 of an integrated chip corresponding to act 712.

As shown in cross-sectional view 1200, a high-k dielectric layer 1202 is formed over the buried oxide layer 1106 and over the active silicon layer 802. In some embodiments, the high-k dielectric layer 1202 may also be deposited along the top surface 1106t of the buried oxide layer 1106. The high-k dielectric layer 1202 may be deposited by way of a vapor deposition process (e.g., PVD, ALD, CVD, PE-CVD). In some embodiments, the high-k dielectric layer 1202 may comprise one or more of silicon nitride ($Si_3N_4$), aluminum oxide ($Al_2O_3$), titanium oxide ($TiO_2$), hafnium oxide (HfO), tantalum pentoxide ($Ta_2O_5$), tin oxide (SnO), tin dioxide ($SnO_2$), $Ba_xSr_1-xTiO_3$ (BST).

Figure 13:
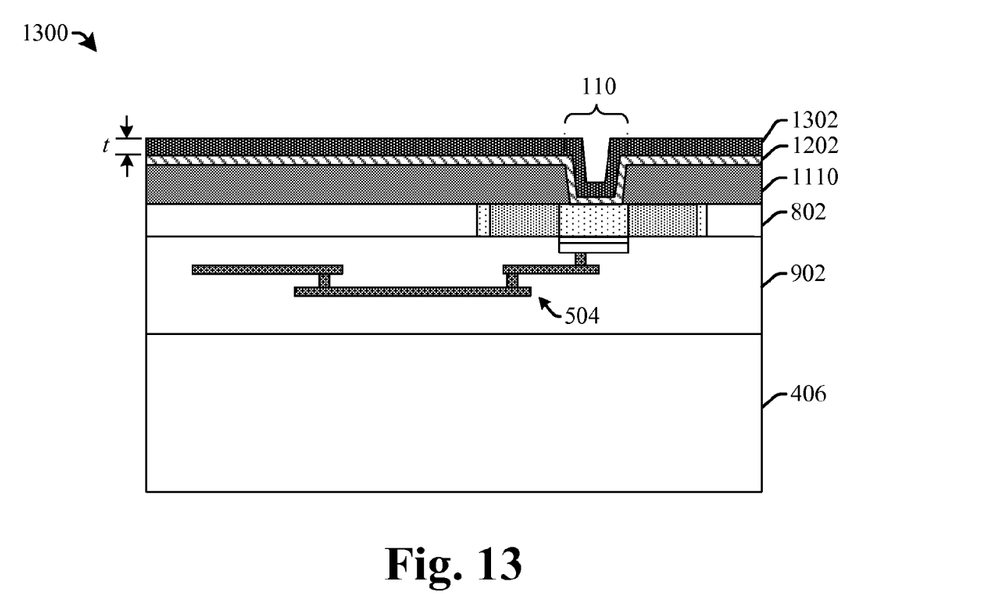

FIG. 13 illustrates some embodiments of a cross-sectional view 1300 of an integrated chip corresponding to act 714.

As shown in cross-sectional view 1300, a sensing well spacer layer 1302 is formed onto the high-k dielectric layer 1202. The sensing well spacer layer 1302 may be formed by way of a vapor deposition process (e.g., PVD, ALD, CVD, PE-CVD) to a thickness t in a range of between approximately 50 nm and approximately 250 nm. The sensing well spacer layer 1302 is deposited onto interior surfaces of the sensing well 114. The sensing well spacer layer 1302 comprises a material having a high etching selectivity with respect to the high-k dielectric layer 410. For example, the sensing well spacer layer 1302 may etch at a rate that is greater than 5 times larger than the rate at which the high-k dielectric layer 410 etches. In some embodiments, the sensing well spacer layer 1302 may comprise a nitride (e.g., silicon nitride) or an oxide.

Figure 14:
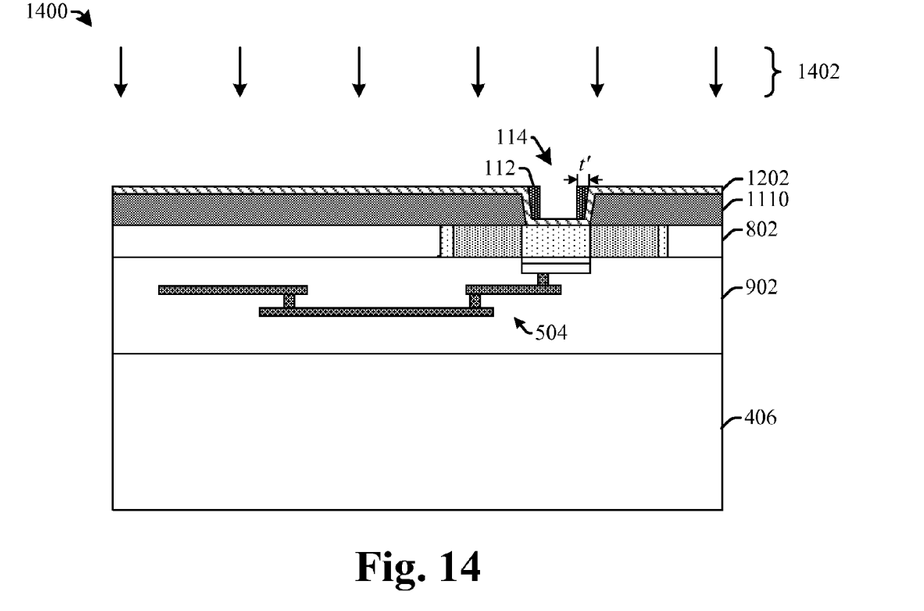

FIG. 14 illustrates some embodiments of a cross-sectional view 1400 of an integrated chip corresponding to act 716.

As shown in cross-sectional view 1400, the sensing well spacer layer (e.g., 1302 of FIG. 13) is exposed to an etchant 1402 that removes the sensing well spacer layer from horizontal (i.e., lateral) surfaces to form one or more sensing well spacers 112 that define a sensing well 114. Removing the sensing well spacer layer from horizontal surfaces leaves the one or more sensing well spacers 112 on sidewalls of the sensing well 114. The thickness t' of the one or more sensing well spacers 112 depends upon the thickness t of the sensing well layer (e.g., 1302 of FIG. 13). Therefore, a size of the sensing well 114 may be controlled by controlling the thickness t of the sensing well layer (e.g., 1302 of FIG. 13).

Figure 15:
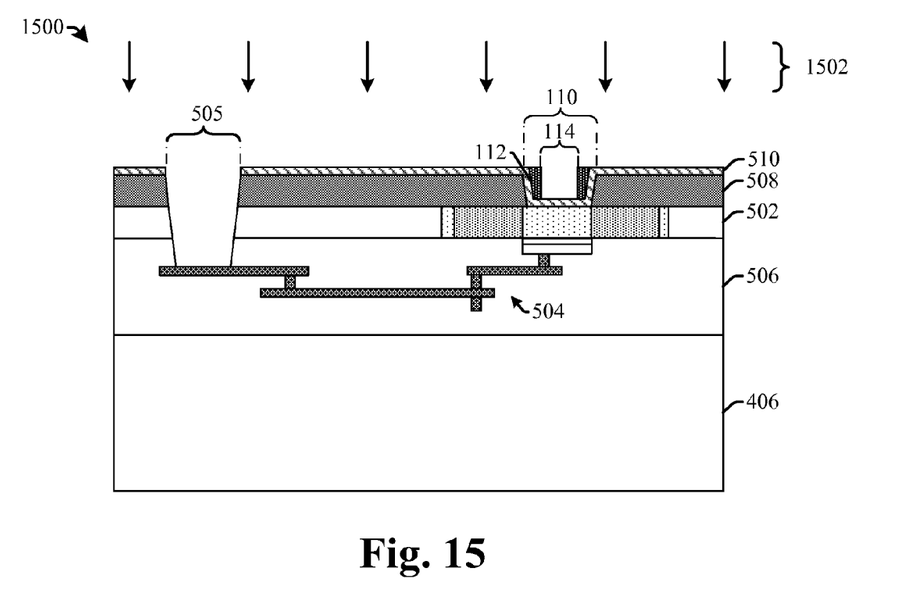

FIG. 15 illustrates some embodiments of a cross-sectional view 1500 of an integrated chip corresponding to act 718.

As shown in cross-sectional view 1500, the SOI substrate is selectively exposed to an etchant 1502 that forms a wire-bonding well 505 within the SOI substrate. The wire-bonding well 505 vertically extends from a top of the buried oxide layer 508, through the active silicon layer 502, to one of the plurality of metal interconnect layers 504 within ILD layer 506. In some embodiments, the etchant 1502 may comprise a dry etchant have an etching chemistry comprising a fluorine species (e.g., $CF_4$, $CHF_3$, $C_4F_8$, etc.), oxygen, and/or hydrogen, for example. In other embodiments, the etchant 1502 may comprise a wet etchant comprising hydroflouric acid (HF).

Figure 16:
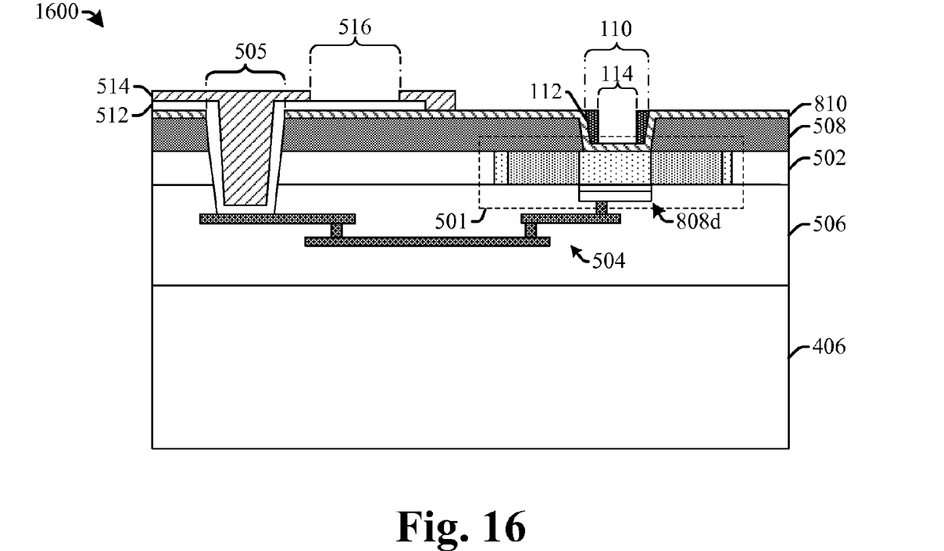

FIG. 16 illustrates some embodiments of a cross-sectional view 1600 of an integrated chip corresponding to act 720.

As shown in cross-sectional view 1600, a wire-bond redistribution layer 512 is formed to extend from a position within a wire-bonding well 505 to a position overlying the buried oxide layer 508. The wire-bond redistribution layer 512 is configured to provide for a conductive path that extends from a bottom of the wire-bonding well 505 to a top of the buried oxide layer 508. The wire-bond redistribution layer 512 may comprise a conductive material (e.g., tungsten or copper) deposited by way of a vapor deposition technique (e.g., physical vapor deposition, chemical vapor deposition, etc.). The plurality of metal interconnect layers 504 are configured to electrically connect the wire-bond redistribution layer 512 to the integrated bio-sensor 501. For example, the plurality of metal interconnect layers 504 may laterally connect the wire-bond redistribution layer 512 to the gate region 808d of the integrated bio-sensor 501, by way of one or more metal wires, metal vias, and a contact.

One or more dielectric structures 514 may be subsequently formed onto the wire-bond redistribution layer 512. The one or more dielectric structures 514 define a wire-bonding area 516 overlying the wire-bond redistribution layer 512. In some embodiments, the one or more dielectric structures 514 may comprise silicon dioxide ($SiO_2$) deposited by way of a vapor deposition technique (e.g., physical vapor deposition, chemical vapor deposition, etc.).

Figure 17:
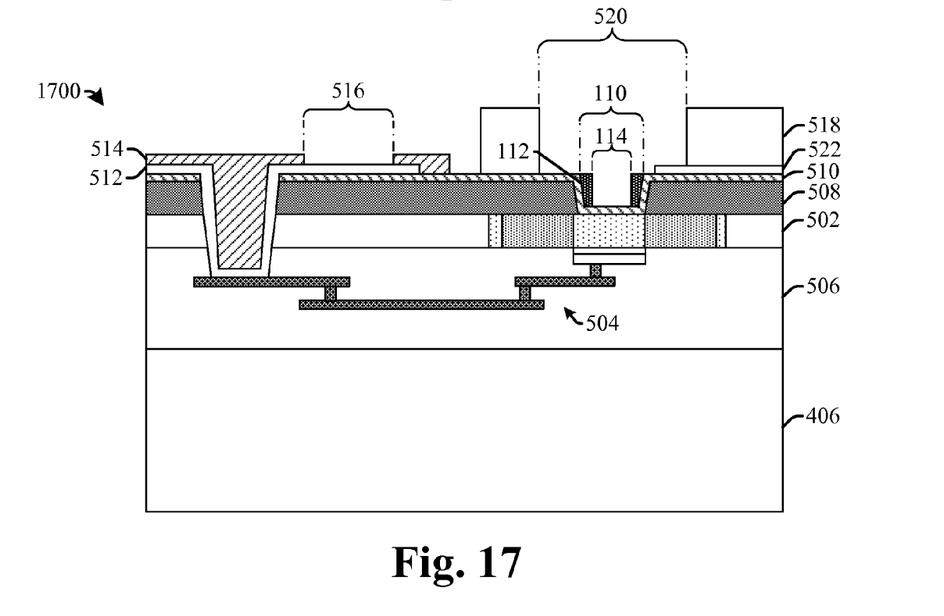

FIG. 17 illustrates some embodiments of a cross-sectional view 1700 of an integrated chip corresponding to act 722.

As shown in cross-sectional view 1700, a fluidic channel 520 is arranged over the sensing well 114. The fluidic channel 520 may be defined by one or more channel definition structures 518. The one or more channel definition structures 518 may be formed by selectively forming a polymer onto the high-k dielectric layer 510. For example, polydimethylsiloxane (PDMS) may be spin-coated onto the high-k dielectric layer 510, then cured (e.g., heated at an elevated temperature), and then selectively patterned using photolithography and etch processes. In some embodiments, a conductive layer 522, configured to act as a front gate electrode for a DG ISFET, may be formed onto the high-k dielectric layer 510 prior to the formation of the one or more channel definition structures 518.

Therefore, the present disclosure relates to an integrated chip having an integrated bio-sensor with a sensing well comprising one or more sensing well spacers that are configured to reduce a size of the sensing well after its formation In some embodiments, the present disclosure relates to an integrated chip having an integrated bio-sensor. The integrated chip comprises a sensing device disposed within a semiconductor substrate. A dielectric structure is disposed onto a first side of the semiconductor substrate. The dielectric structure overlies the sensing device and has an opening that is exposed to an ambient environment. The opening has a first width. The integrated chip further comprises one or more sensing well spacers arranged on sidewalls of the opening. The one or more sensing well spacers expose a bottom surface of the opening to define a sensing well having a second width that is smaller than the first width.

In other embodiments, the present disclosure relates to an integrated chip having an integrated bio-sensor. The integrated chip comprises a transistor device disposed within an active silicon layer and having a source region and a drain region that are laterally separated by a channel region. The integrated chip further comprises a buried oxide layer disposed onto a first side of the active silicon layer and having an opening that overlies the transistor device and that is exposed to an ambient environment. The opening has a first width. The integrated chip further comprises a high-k dielectric layer disposed onto interior surfaces of the opening. The integrated chip further comprises one or more sensing well spacers arranged on sidewalls of the opening at positions that are laterally separated from the buried oxide layer and that are vertically separated from the transistor device by the high-k dielectric layer. The one or more sensing well spacers expose a bottom surface of the opening to define a sensing well that overlies the channel region and is laterally set back from the source region and the drain region.

In yet other embodiments, the present disclosure relates to a method of forming an integrated chip having an integrated bio-sensor. The method comprises forming a sensing device within a semiconductor substrate. The method further comprises forming a dielectric structure over the semiconductor substrate. The method further comprises selectively etching the dielectric structure to form an opening that overlies the sensing device and that is exposed to an ambient environment, wherein the opening has a first width. The method further comprises forming one or more sensing well spacers onto sidewalls of the opening, wherein the one or more sensing well spacers expose a bottom surface of the opening to define a sensing well having a second width that is smaller than the first width.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. An integrated chip having an integrated bio-sensor, comprising:
   a sensing device disposed within a semiconductor substrate;
   a dielectric structure disposed onto a first side of the semiconductor substrate and having an opening that overlies the sensing device, wherein the opening has a first width; and
   one or more sensing well spacers confined within the opening and arranged on sidewalls of the opening, wherein a second opening is arranged between sidewalls of the one or more sensing well spacers and extends through the one or more sensing well spacers to define a sensing well having a second width that is smaller than the first width; and
   wherein a high-k dielectric layer is disposed within the sensing well and is laterally between the one or more sensing well spacers and the dielectric structure and vertically between the one or more sensing well spacers and the sensing device.

2. The integrated chip of claim 1,
   wherein the high-k dielectric layer contacts the one or more sensing well spacers and the dielectric structure.

3. The integrated chip of claim 1, wherein the high-k dielectric layer further abuts a top surface of the dielectric structure that opposes the semiconductor substrate.

4. The integrated chip of claim 1, wherein the one or more sensing well spacers comprise a material that etches at a faster etching rate than the high-k dielectric layer.

5. The integrated chip of claim 1, wherein the one or more sensing well spacers comprise a nitride or an oxide.

6. The integrated chip of claim 1,
   wherein the sensing device comprises a source region and a drain region, which are laterally separated by a channel region; and
   wherein the sensing well overlies the channel region and is laterally set back from the source region and the drain region.

7. The integrated chip of claim 1, further comprising:
   a plurality of metal interconnect layers arranged within an inter-level dielectric (ILD) layer disposed onto a second side of the semiconductor substrate opposing the first side of the semiconductor substrate.

8. The integrated chip of claim 7, further comprising:
   a wire-bonding well laterally separated from the sensing device and vertically extending from a top surface of dielectric structure to a location within the ILD layer that abuts one of the plurality of metal interconnect layers.

9. The integrated chip of claim 8, further comprising:
   a wire-bond redistribution layer comprising a conductive material that extends from a first position abutting the one of the plurality of metal interconnect layers to a second position overlying the dielectric structure.

10. An integrated chip having an integrated bio-sensor, comprising:
    a transistor device disposed within an active silicon layer and having a source region and a drain region that are laterally separated by a channel region;

a buried oxide layer disposed onto a first side of the active silicon layer and having an opening that overlies the transistor device, wherein the opening has a first width;
a high-k dielectric layer disposed within the opening; and
one or more sensing well spacers arranged on sidewalls of the high-k dielectric layer at positions that are vertically separated from the transistor device by the high-k dielectric layer, wherein a second opening is arranged between sidewalls of the one or more sensing well spacers and extends through the one or more sensing well spacers to the high-k dielectric layer to define a sensing well that overlies the channel region and is laterally set back from the source region and the drain region.

11. The integrated chip of claim 10, wherein the high-k dielectric layer further abuts a top surface of the buried oxide layer opposing the active silicon layer.

12. The integrated chip of claim 10, wherein the one or more sensing well spacers comprise a material that etches at a faster etching rate than the high-k dielectric layer.

13. The integrated chip of claim 10, further comprising:
a plurality of metal interconnect layers arranged within an inter-level dielectric (ILD) layer disposed onto a second side of the active silicon layer opposing the first side of the active silicon layer.

14. The integrated chip of claim 13, further comprising:
a wire-bonding well laterally separated from the transistor device and vertically extending from a top surface of buried oxide layer to a location within the ILD layer that abuts one of the plurality of metal interconnect layers; and
a wire-bond redistribution layer comprising a conductive material that extends from a first position abutting the one of the plurality of metal interconnect layers to a second position overlying the buried oxide layer.

15. An integrated chip, comprising:
a transistor device disposed within an active layer and having a source region and a drain region separated by a channel region;
a dielectric layer disposed over the active layer and having an opening that overlies the transistor device;
a high-k dielectric layer disposed onto the channel region, onto sidewalls of the opening, and onto an upper surface of the dielectric layer facing away from the active layer; and
one or more sensing well spacers comprising a dielectric material arranged within the opening at positions separated from the dielectric layer and the transistor device by the high-k dielectric layer.

16. The integrated chip of claim 15, wherein a second opening is arranged between sidewalls of the one or more sensing well spacers and extends through the one or more sensing well spacers to the high-k dielectric layer.

17. The integrated chip of claim 15, wherein the one or more sensing well spacers have upper surfaces that are substantially co-planar with an upper surface of the high-k dielectric layer.

18. The integrated chip of claim 15, wherein the opening has angled sidewalls that cause a width of the opening to increase as a distance from the active layer increases.

19. The integrated chip of claim 15, further comprising:
a wire-bonding well laterally separated from the opening and extending through the high-k dielectric layer, the dielectric layer, and the active layer.

20. The integrated chip of claim 15, further comprising:
a plurality of metal interconnect layers arranged within an inter-level dielectric (ILD) layer disposed onto an opposite side of the active layer as the high-k dielectric layer.

* * * * *